(12) United States Patent
Moradi et al.

(10) Patent No.: US 8,663,584 B2
(45) Date of Patent: Mar. 4, 2014

(54) METHOD AND TECHNIQUE EMPLOYING A NOVEL EXTRACTANT TO ENHANCE RECOVERY OF GOLD AND PALLADIUM FROM HYDROCHLORIC ACID MEDIA

(76) Inventors: Loghman Moradi, Sanandaj (IR); Hiwa Salimi, Sanandaj (IR); Mohammad Piltan, Sanandaj (IR); Issa Yavari, Tehran (IR)

( * ) Notice: Subject to any disclaimer, the term of this patent is extended or adjusted under 35 U.S.C. 154(b) by 0 days.

(21) Appl. No.: 13/042,245

(22) Filed: Mar. 7, 2011

(65) Prior Publication Data
US 2012/0228151 A1    Sep. 13, 2012

(51) Int. Cl.
*C01G 7/00*    (2006.01)
(52) U.S. Cl.
USPC ............................................. 423/22; 423/24
(58) Field of Classification Search
USPC .......... 423/22, 24; 75/714, 744; 205/569, 570
See application file for complete search history.

(56) References Cited

U.S. PATENT DOCUMENTS

| | | | | |
|---|---|---|---|---|
| 5,284,633 | A * | 2/1994 | Gefvert | 423/22 |
| 7,291,202 | B2 * | 11/2007 | Asano et al. | 75/741 |
| 7,597,863 | B2 * | 10/2009 | Narita et al. | 423/22 |

* cited by examiner

*Primary Examiner* — Steven Bos
(74) *Attorney, Agent, or Firm* — Donn K. Harms

(57) ABSTRACT

An extraction component enabling the concurrent recovery of gold and/or palladium selectively from a hydrochloric acid media containing the base metals and other contaminants. The disclosed extractant disclosed eliminates the conventional multi-step process for such extraction by providing for an extraction method which uses a single solvent extraction reagent. Further enhancing the conventional multi step process, the conventional scrubbing stage is eliminated by a single stripping stage. The resulting solutions can be obtained from leaching many types of material such as copper anode slimes, the treatment of scrap such as electronic circuit boards and plating effluents, PGM, or refractory gold ores.

13 Claims, 2 Drawing Sheets

METHOD AND TECHNIQUE EMPLOYING A NOVEL EXTRACTANT TO ENHANCE RECOVERY OF GOLD AND PALLADIUM FROM HYDROCHLORIC ACID MEDIA

BACKGROUND OF THE INVENTION

1. Field of the Invention

This invention relates to a method and material employed for recovery of palladium and gold from base metals and impurities. More particularly it relates to a system and method employing a single novel extractant in a method allowing for extraction of palladium and gold from acidic media containing chloride ions.

2. Prior Art

Throughout the world, for centuries, their has been a continuing demand for precious metals. In earlier times such was desirable for decorative purposes and as a means to store wealth of regents. More modernly, in addition to decorative purposes, precious metals are employed throughout the world in products such as electronics. With the ongoing metamorphosis of countries like China into high technology manufacturers and consumers, there continues to be an ever increasing industrial demand for precious metals. The increasing industrial use, and increased ownership by individuals and governments during current economic times, has driven the price for precious metals to historic highs.

Mining of precious metals has become prohibitively costly and the minerals extracted by mining is unable to keep up with the logarithmic increase in demand. The above noted increased ownership and use, and the lessening supply from mined sources of precious metals, and the resulting high prices for such metals, has made the processes of recovering and refining these metals from other underused sources, potentially a very significant source, if they can be extracted and delivered at reasonable prices through refining and extracting of underutilized sources already existing.

Copper anode slime is one of the major sources of the precious metals. Copper anode slime occurs in copious quantities during copper smelting. The anode slime collects at the bottom of conventional electrolytic copper refining cells. This anode slime contains significant quantities of platinum group metals especially platinum and palladium. The slime also contains significant quantities of gold, silver, aluminum, zinc, copper, arsenic, selenium, tellurium, nickel, and iron.

Smelting firms are cognizant of the slime contents and conventionally employ a solvent extraction process to the anode slime to achieve a concentration, separation, and final extraction of precious metals by these large industrial companies. Despite simplicity and other advantages of solvent extraction process in precious metals recovery from copper anode slime, serious problems associated with the process exist which must be solved.

Major impediments to the reagent used in such solvent extraction processes of precious metals exist in the recovery procedure, including extraction and stripping rate, extractant consumption, and selectivity. Two conventional extractants employed in this process include Dibutyl carbitol (DBC) and di-n-hexyl sulfide (DHS). These are employed as preferred extractants to yield gold and palladium respectively in the extraction process from sources such as copper anode slime. Prior art has sought to solve some of these problems without significant success.

U.S. Pat. No. 7,291,202 describes the extraction of 1 mol gold from PGM concentrate by employing about 75 mol DBC. The extraction time using this quantity of DBC is taught at about 10 minutes. As taught in this patent, the extraction of gold with DBC from the subject material required five different stages. The process employed 2 stages for initial extraction, and three stages of scrubbing are then employed using 5 M hydrochloric acid solutions. This method involves problems, one of which is the large amount of extractant DBC used for extraction of gold for the ten minute time duration. Further, the taught method requires multi-steps for both extraction and for scrubbing stages. It is thus time consuming and expensive due to the amount of labor and extractant material that is used. Further, the conventional palladium extractant (DHS) taught for use for extraction of palladium to yield a molar ratio of 6:1 (DHS:Pd) requires no less than 3 hours of time. The '202 patent describes that gold disturbs the extraction of palladium with DHS. Thus for extraction of palladium by DHS, gold must be removed at first because DHS cannot extract gold and/or palladium simultaneously. Consequently, there is a major drawback of DHS employed as an extractant since it yields a very low extraction kinetic and is time consuming.

U.S. Pat. No. 5,284,633 teaches a new technique for separating of gold, palladium and platinum from the available material such as anode slime. This patent teaches the use of a single extractant, kelex 100, to be employed as the extraction reagent. However the '633 patent has some serious flaws also.

First, using the method and extractant of the '633 patent, yields a low extraction of precious metals using a feed solution which is employed in a high volume. The extractant consumption for recovery of precious metals from the taught feed solution used of substantially 200 mol of kelex 100 yields only 1 mol of recovered precious metal. Using this 200:1 ratio, the extraction time takes at least 2 minutes. Further, because the employment of kekex 100 also extracts iron to the organic phase at a taught ratio of 27%, it requires scrubbing and the scrubbing process in each stage eliminates a portion of the precious metals which are being recovered, from the organic phase (Au: 3%, Pt: 6% and Pd: 2%) thereby increasing cost from lower yields.

U.S. Pat. No. 7,597,863 teaches the utilization of sulfur containing diamide agents for the extraction of palladium. In the '863 patent, it is taught that 200 mol the extractant must be employed to yield a recovery of 1 mol palladium. Using this costly 200:1 ratio is especially time consuming as it lasts at least 10 minutes. The '863 thus has some major disadvantages since it requires a very high consumption of the extractant for the low yield, and it uses a hydrochloric acid solution containing thiourea in the eventual stripping stage which is conventionally not considered suitable for practical widespread application. Due to some shortages of the ingredients of this and other above noted extractants, costs are increased and production slowed.

As such, there exists an unmet need for a more effective and economical system employing a more practical reagent in the extraction of precious metals from sources such as copper anode slime and the like. Such a method should yield the highest amount of recovered precious metal with a significantly lower utilization of extractant than current systems. Finally, thus a system and extractant should significantly reduce the time needed for the process by the elimination of time-consuming scrubbing stages so that production may speed up and further lower costs by increasing valuable recovered precious metals using less labor and extractant material.

SUMMARY OF THE INVENTION

The noted shortcomings of the prior art are solved in the disclosed method and system herein. The disclosed method and used materials herein provide a procedure allowing for selective extraction and concentrating of gold and palladium from acidic solutions containing chloride ions. The system herein employs a solvent extraction process using the herein disclosed novel extractant. The disclosed extractant employs derivatives of dithiobiuret as a means to simultaneously extract gold and palladium from acidic solutions containing chloride and base metal ions derived from leaching of ores, catalysts, anode slimes or other such materials containing precious metals. The process is further enhanced because it allows for a loaded organic phase during the recover without a scrubbing stage. This one step process using a single solvent extraction reagent requiring only a single stripping stage eliminates the need for a costly scrubbing stage.

As will be seen in this disclosure, a number of improvements in the process itself and the extractant are provided by the disclosed method and extractant. Of particular note, the disclosed extractant is very selective for extraction of gold and palladium even when employed in the presence of contaminants. Thus the high percentage of extraction of gold and palladium (about 99.9%) can be achieved in one stage.

Also of note, the extraction kinetic of palladium and gold by utilizing disclosed extractant is much faster than conventional methods and works I substantially two minutes in many cases. This exceeds in the conventional DRS commercial extractant for extraction of palladium which has an extraction time of 180 minutes. Thus the extraction of gold and palladium with the disclosed extractant enabling the disclosed method is time and energy saving.

Further, the disclosed extractant can extract both gold and palladium simultaneously. This eliminates the conventional need to utilize different extractants separately for the respective metals and reduces the cost of metal recovery process.

Still further, due to a high selectivity of the disclosed extractant, the process does not require the conventional scrubbing stage. This results in significant monetary savings for energy and ecological benefits. Additionally ecologically beneficial is the fact that the disclosed extractant is very stable in extraction conditions and thus it can be re employed many times without significant loss of extraction ability.

Also, a high concentration of gold and palladium can be achieved in the organic phase without utilizing any modifier as is required conventionally. Because of high selectivity and high loading capacity the disclosed extractant can be employed in single batch method at an aqueous to organic ratio of 6:1 instead of multi-step counter-current contacts of conventional methods. Thus the amount of solvent used in the disclosed system is substantially less than systems using conventional solvent extractants.

Especially attractive to many countries and firms not having high technical expertise is the fact that the synthesis of the disclosed extractant is simple and the cost of synthesis process is very low, versus conventional commercial extractants (DRS and DBC). As such, due to aforementioned advantages of the disclosed extractant and resulting method, a significant improvement is yielded in both economic considerations, and economy, and it has the potential to revolutionize the industry of precious metals recovery.

With respect to the above description, it is to be understood that the invention and method herein, is not limited in its application to the details of construction and to the arrangement of the components in this specification or illustrated in the drawings showing metals extraction method herein. The disclosed method herein described and extractant disclosed, provides a novel one step precious metals recovery system, is capable of other embodiments and of being practiced and carried out in various ways which will be obvious to those skilled in the art upon reading this disclosure. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other improved precious metal extraction processes. It is important, therefore, that the claims and disclosure herein be regarded as including any such equivalent construction and methodology insofar as they do not depart from the spirit of the present invention.

It is an object of this invention to provide a method and means for precious metal extraction which conserves time and yields increased production of precious metals.

An additional object of this invention is the provision of a precious metals extraction system and a metals extraction process which allows for a loaded organic phase during the recovery without a scrubbing stage.

Yet another object of this invention is the provision of a metals extraction process which is a one step process using a single solvent extraction reagent and only requiring only a single stripping stage.

These together with other objects and advantages which become subsequently apparent, reside in the details of the construction and operation as herein described with reference being had to the accompanying drawings forming a part thereof, wherein like numerals refer to like parts throughout.

BRIEF DESCRIPTION OF DRAWING FIGURES

DETAILED DESCRIPTION OF PREFERRED EMBODIMENTS OF THE INVENTION

Figure 1:
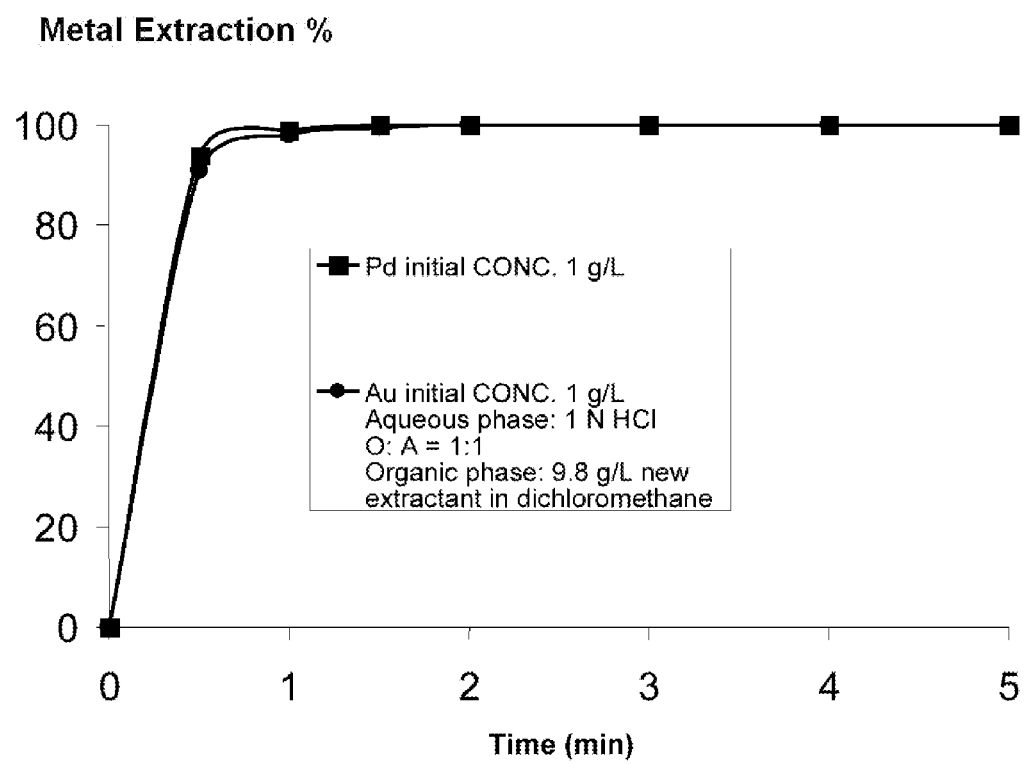
FIG. 1 is a drawing showing a dependence of gold and palladium extraction percentage, employing conventionally used extractants, such as DHS, depicting an extraction time.
Figure 2:
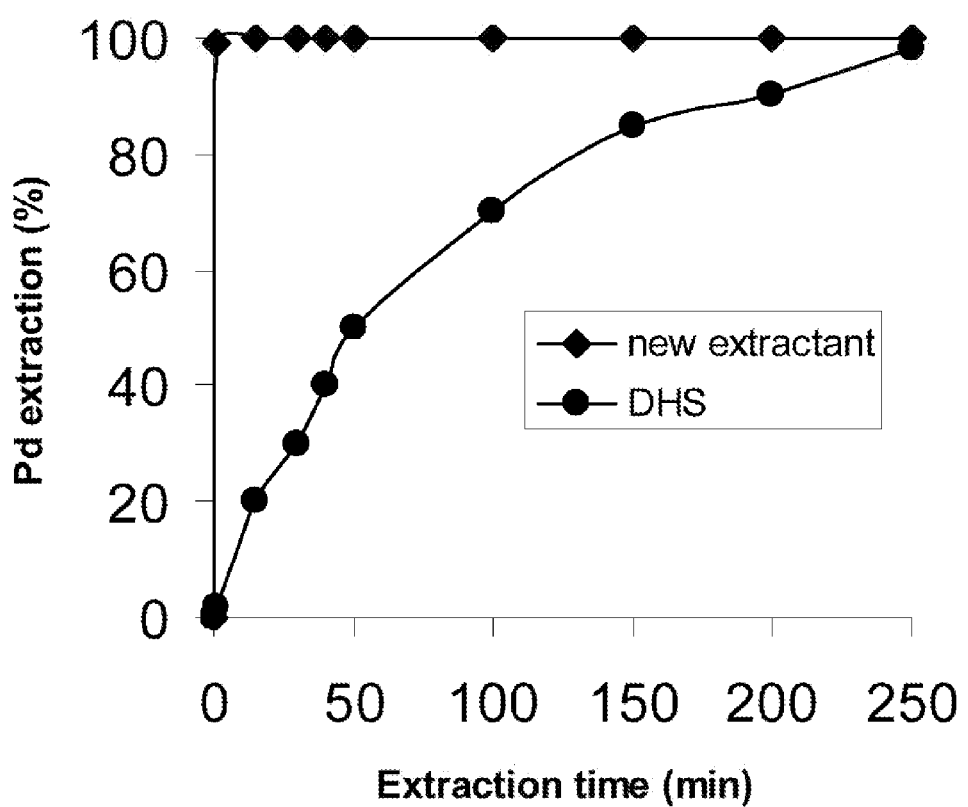
FIG. 2 is a graph depicting the increased extraction efficiency employing the disclosed exctractant and method herein.

As disclosed herein the novel extraction component disclosed and described herein, enables a method of recovering gold and palladium selectively from hydrochloric acid media containing base metals and other contaminants. The novel extractant disclosed provides for a time and labor saving method which uses a single solvent extraction reagent. Further enhancing the conventional multi step process, only a single stripping stage is required wherein the scrubbing stage of conventional processing is eliminated as it is not required.

The extracting agents disclosed, employed by method disclosed in this invention, can form considerably stronger complexes with the gold and palladium than with base metals. The acidic solution containing chloride ion can be achieved by leaching a material which includes the desired precious metals, by adding an acid containing an oxidizing agent. The resulting solutions can be obtained from leaching many types of material such as copper anode slimes; treatment of scrap such as electronic circuit boards; plating effluents, PGM or refractory gold ores.

Copper anode slimes conventionally contain varying quantities precious metals such as gold, platinum, palladium and silver. Other contents includes copper, selenium, tellurium, lead, arsenic, antimony, nickel, iron, cobalt, barium, aluminum, zinc, etc.

In the precious metals recovery process herein disclosed employing the disclosed novel extracting agent with an anode slime, the process includes in a first stage of leaching the copper anode slime with nitric acid 8-10 M (2 times) for about 2 hours at 85° C., or till a solute is reached at least about 95% by weight of the silver content and efficient oxidization of precious metals, in hydrochloric acid leaching stage. Next, the leaching residue is separated from the lechate.

After separating the leaching residue from the lechate, the leaching residue is leached by mixture of hydrochloric acid and hydrogen peroxide to form a slurry. This slurry so formed, is then filtered to separate a leaching residue from a desirable leachate containing gold, platinum, palladium and other base metals. Oxidizing is then accomplished employing one or a combination of different oxidizing agents such as chlorine, perchlorate, permanganate, hydrogen peroxide etc. The use of HCl as the leaching solution and H2O2 as the oxidizing agent is preferred.

Following this adjustment step of the liquid characteristics of the leachate, a solvent extraction step is employed using the disclosed novel extractant herein. This extraction step is employed to extract gold and palladium from the leachate. The resulting loaded organic is then stripped with acidified thiourea solution, without the need for the conventional scrubbing stage of conventional extraction methods. This stripping yields a substantially yellow precipitate containing palladium along with a solution containing gold free of base metals which is obtained.

In this method, palladium is selectively separated from gold in a stripping stage without the need to use conventional multiple reagents. As described above, extraction of the precious metals by the method herein enabled by the disclosed novel extractant, thus is very time and energy saving.

One important enhanced feature of the present invention is that the employment of the disclosed extracting agent eliminates all of the impurities in the extracting stage without using scrubbing process. Palladium and gold are thus extracted concurrently from this acidic feed solution by using the single disclosed extractant instead of a plurality of extractants in the conventional mode of the extraction process.

Still further, the disclosed extractant is reusable at least 15 times after the striping stage. It thus may be employed for subsequent extraction of the precious metals from new feed liquors, without damaging and decreasing power of extraction method herein.

In solvent extraction techniques, single batch extraction and high loading capacity of the extractant have important roles. The results obtained from example 8, disclose that the organic phase employing the disclosed extractant herein, in the absence of any modifiers, can be extremely loaded with precious metals in a single batch process without the solvent becoming viscose. Consequently, the solvent consumption in the disclosed method employing the novel extractant, uses significantly less solvent and extractant than conventional methods.

The disclosed extracting agent used in present invention and method, is a new derivative of dithiobiuret having substantially the following formula:

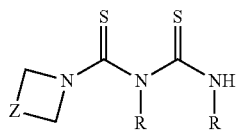

In the above formula, R is cyclohexyl or isopropyl and Z represents a group consist of —CH2-, —CH2-CH2-, CH2-CH2-CH2, CH2-CH(CH3)-CH2, CH2(CH2)2CH2, CH2-NH—CH2-, CH2-CHOH—CH2-, CHOH—CH2-CH2-, —CH2-O—CH2-.

More importantly, this extracting agents introduced herein are able to form very stable chelates with gold and palladium which eliminates the base metal contaminants in the conventional solvent extraction process without needing to scrubbing step before stripping stage. Then in the stripping stage, the said precious metals are selectively recovered utilizing an acidified thiourea solution. The organic solvents that can be used in this process are including of polar hydrocarbon solvents such as dichloromethane, dichloroethane, chloroform, esters such as ethyl acetate, chlorobenzene and 1,2 dichlorobenzene etc.

The acidified thiourea solution used in this process can have an acid concentration of from about 0.5-2 M, more preferably from about 0.5-1 M of HCl, HNO3, H2SO4, that the sulfuric acid is preferred. Additionally, the acidified thiourea solution may contain from about substantially 0.3-1M of thiourea, such that the concentration of 0.7 mol of thiourea is preferably achieved.

Utilizing of acidified thiourea for stripping of precious metals from the dithiobiuret complex doesn't damage the organic phase in contrast to other conventional stripping methods taught reported in the prior arts such as hydrolytic or direct hydrogen reduction. The disclosed herein, single solvent extraction process which is combined with a single stripping stage and recycling of extractant several times will thus provide a means to decrease the total cost of precious metal recovery. Furthermore, the strip solutions obtained by this process can be treated chemically to recover gold by electrolyze or reduced with hydrogen or sodium borohydride to produce gold powders.

The following examples are given to illustrate the employment of the method and extractant disclosed in the invention herein.

EXAMPLE 1

Typical procedure for preparation of the preferred novel extractant: The 0.55 kg of CS2 was added in small portions over a period of about 1 hour to a mixture of 0.48 kg morpholine amine and 1 kg dicyclohexyl carbodiimide (DCC) in 6 L of methanol at 10° C. or less. The reaction mixture was stirred for 4 hours. When the reaction was completed, the precipitated solid was removed by filtration and washed with water two times. This product is easily recrystallized from methanol. This reaction can be carried out in water or solvent free conditions too.

EXAMPLE 2

1 L organic solution containing of 4.5 g new extractant in dichloromethane, was contacted vigorously with an equal volume of 0.5 M hydrochloric acid solution containing 2000 ppm gold in form of gold chloride (AuCl4-). After a contact time of 90 sec the phases were allowed to separate. After extraction, the aqueous phase is analyzed by AAS (Atomic Absorbance Spectroscopy). Based on AAS data, the remained gold in aqueous phase was about 0.6 ppm.

EXAMPLE 3

1 L of organic solution containing 15.3 g new extractant in dichloromethane, was contacted vigorously with an equal volume of 0.5 M of hydrochloric acid solution contain 2000 ppm palladium in form of palladium chloride (PdCl4-2).

After a contact time of 90 sec the phases were allowed to separate. After extraction, the aqueous phase is analyzed by AAS (Atomic Absorbance Spectroscopy). Analysis of the aqueous phase showed that the remained palladium in aqueous phase was about 0.1 ppm.

EXAMPLE 4

1 L of organic solution containing 8.5 g new extractant in dichloromethane was contacted vigorously with an equal volume of 0.5 M HCl containing 10000 ppm barium, 10000 ppm iron, 4000 ppm aluminum, 4000 ppm nickel, 4000 ppm copper, 4000 ppm zinc, 4000 ppm cobalt, 1000 ppm gold, 30 ppm palladium and 30 ppm platinum. After a contact time of ten minutes the phases were allowed to separate. After extraction, the raffinate and aqueous stripping solution is analyzed by AAS (Atomic Absorbance Spectroscopy). The results are shown in table 1.

TABLE 1

| | Metal (ppm) | | | | | | | | | |
|---|---|---|---|---|---|---|---|---|---|---|
| | Al | Ba | Fe | Cu | Zn | Co | Ni | Au | Pd | Pt |
| Feed | 4000 | 10000 | 10000 | 4000 | 4000 | 4000 | 4000 | 1000 | 30 | 30 |
| Raffinate | 4000 | 10000 | 10000 | 4000 | 4000 | 4000 | 4000 | 0.6 | 0 | 28 |
| Stripping Solution | 0 | 0 | 0 | 0 | 0 | 0 | 0 | 989 | 0.5 | 0.2 |

Table 1 shows that gold and palladium are extracted selectively in to organic phase. The platinum and other base metals remain almost completely in the raffinate.

EXAMPLE 5

0.5 L of loaded organic phase containing 2000 ppm gold earned from example 2 was contacted with equal volume of 0.5 M thiourea solution containing 98 gpl sulfuric acid for 5 minutes at room temperature. The earned analysis data showed complete stripping of gold.

EXAMPLE 6

0.5 of loaded organic phase containing 2000 ppm palladium earned from example 3 was contacted with equal volume of 0.5 M thiourea solution containing 98 gpl sulfuric acid for 5 minutes at room temperature. After stripping a yellow precipitate was obtained. The palladium powder was recovered by calcining the yellow precipitate at 850° C. for 2 hours.

EXAMPLE 7

1 L of organic solution containing 3 g of novel extractant said in example 1, in dichloromethane, was contacted vigorously with an equal volume of 0.5 M hydrochloric acid solution containing 1000 ppm gold in form of gold chloride (AuCl4-). After a contact time of 2 minutes the phases were allowed to separate. The loaded organic phase was contacted with equal volume of 0.5 M thiourea solution containing 98 gpl sulfuric acid for 5 minute, and after separation of two phases, the organic phase was resent for extraction of gold from a new aqueous feed solution, and this procedure was repeated for 15 times. Analysis of final raffinate solution with AAS showed that the remained gold in aqueous phase is about 8 ppm.

EXAMPLE 8

Loading Capacity 1.2 L of a 1 M hydrochloric acid solution contain 13500 ppm palladium in form of palladium chloride (PdCl4-2) was contacted with a 0.2 L dichloromethane containing 80 g of new extractant said in example 1. After a contact time of 3 minutes the phases were allowed to separate. Aqueous phase analyses showed almost completely extraction of palladium in to organic phase. So extremely high concentration of palladium can be extracted in to the organic phase without the solvent becoming immoderately viscous and a single batch extraction can be used for efficient extraction instead of multi-step counter-current contacts.

EXAMPLE 9

Following mixing of 1.5 kg of copper anode slime (comprising of: 1650 ppm for gold, 60 ppm for palladium, 60000 ppm for copper, 700 ppm for iron, 450 ppm for nickel, 9100 ppm for arsenic, 80300 ppm for selenium, 9500 ppm for tellurium, 60000 ppm for silver, 10000 ppm for lead and other impurities) in 1.5 L of hydrochloric acid and 0.7 L of water, 0.5 L of hydrogen peroxide was added gradually to the mixture and the temperature of the liquid was maintained at 70° C. for 4 hours to effect oxidizing leaching. Following cooling, the chlorination leaching residue was filtered. The respective concentration levels within leach liquor were 1250 ppm for gold, 50 ppm for palladium, and containing very high levels of other impurities. The acid concentration of the filtrate was adjusted to 1 M or less, and lead and silver was precipitated and separated from leach liquor. Then filtrate was mixed with equal volume of dichloromethane containing 35 g new extractant said in example 1. Then the mixture allowed stirring for 20 minutes vigorously at room temperature. The two phases were separated and the respective concentration levels with in the raffinate solution were 0.7 ppm for gold and 0.6 ppm for palladium. The resulting data obviously shows almost completely extraction of gold and palladium from copper anode slime.

EXAMPLE 10

Following 2 time leaching of 1.5 kg copper anode slime said in example 9, with 1.5 L of nitric acid (9 M) at 85° C. for 4 hours, the residue was washed with 0.4 L of water. The solid phase after drying mixed with 1.5 L of hydrochloric acid and 0.5 of water. Then 0.5 L of hydrogen peroxide was added gradually to the mixture and the temperature of the liquid was maintained at 70° C. for 4 hours to effect oxidizing leaching. The respective concentration levels within leach liquor were 1600 ppm for gold, 48 ppm for palladium and high levels of other impurities. Following cooling, the chlorination leaching residue was filtered, the acid concentration of the filtrate was adjusted to 1 M, and the filtrate was mixed with equal volume of dichloromethane containing 25 g new extractant said in example 1. Then mixture allowed stirring vigorously for 20 minutes at room temperature. The two phases were separated and the respective concentration levels with in the raffinate were 0.4 ppm for gold, 0.2 ppm for palladium. The organic phase was stripped with equal volume of 0.5 M thiourea solution containing 98 gpl sulfuric acid for 5 minutes at room temperature. The earned analysis data from the aqueous phase exposed 1750 ppm for gold without any other impurities.

While all of the fundamental characteristics and features of the metal extractant and resulting method herein have been shown and described, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art, without departing from the spirit or scope of the invention. Consequently, all such modifications and variations and substitutions as will certainly occur to those skilled in the art on reading this disclosure, are included within the scope of the invention as defined by the following claims.

What is claimed is:

1. A method of separating at least one of gold and palladium from an acid solution containing chloride complexes of at least one of these metals, said method comprising the steps of:

employing an extractant selected from dithiobiuret derivative compounds represented by the following structure formula:

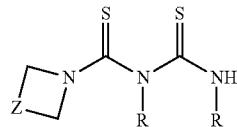

wherein R is cyclohexyl or isopropyl and Z represents a group selected from the group consisting of: —CH$_2$—, —CH$_2$—CH$_2$—, CH$_2$—CH$_2$—CH$_2$, CH$_2$—CH (CH$_3$)—CH$_2$, CH$_2$(CH$_2$)$_2$CH$_2$, CH$_2$—NH—CH$_2$, CH$_2$—CHOH—CH$_2$—, CHOH—CH$_2$—CH$_2$—, and —CH$_2$—O—CH$_2$—; and contacting said acid solution with a quantity of said extractant, for a sufficient length of time to form a loaded organic consisting of either or both of gold and palladium to allow for a single step extraction of substantially all the gold and palladium present.

2. The method of claim 1 additionally comprising: employing a hydrochloric acid solution as said acid solution.

3. The method of claim 2, additionally comprising:
employing the extractant for extraction of at least one of gold and palladium from said hydrochloric acid solution containing Pt, Ba, Al, Cu, Fe, Ni, Zn, Co, and mixtures thereof.

4. The method of claim 3, additionally comprising:
employing said hydrochloric acid solution at a concentration of substantially 1 M HCl.

5. The method of claim 2 with the additional step of:
employing an acidified thiourea solution in a stripping stage to yield a substantially yellow precipitate containing palladium concurrently with a strip solution containing gold which is free of base metals, to concurrently selectively separate said palladium from said gold.

6. The method of claim 5 comprising the additional step of:
employing a treatment of said strip solution to produce gold precipitate, said treatment including one or a combination of electrolysis and reducing said strip solution with hydrogen or sodium borohydride.

7. The method of claim 5 with the additional step of:
separating said extractant to yield recovered extractant from said strip solution for reuse.

8. The method of claim 7 including the additional step of:
employing said recovered extractant with a subsequent new feed solution, said recovered extractant reusable at least 15 times.

9. The method of claim 5, additionally comprising:
employing said acidified thiourea solution containing from substantially 0.5-3 M H2SO4.

10. The method of claim 5, additionally comprising:
employing said acidified thiourea solution containing from substantially 0.5-1 M thiourea.

11. The method of claim 10, additionally comprising:
employing an extraction rate of palladium in acidic aqueous solution of 0.5 M HCl in contact with organic phase of 2.2 mol of said extractant for 1 mol of palladium for 90 seconds.

12. The method of claim 10, additionally comprising:
employing an extraction rate of palladium in acidic aqueous solution of 0.5 M HCl in contact with organic phase of 2.2 mol of said extractant for 1 mol of gold for 90 seconds.

13. The method of claim 1, additionally comprising:
employing said extractant to extract gold and Palladium concurrently and selectively from a copper anode slime in 1M HCL or less.

* * * * *